(12) United States Patent
Hamatani et al.

(10) Patent No.: US 11,708,480 B2
(45) Date of Patent: Jul. 25, 2023

(54) RUBBER COMPOSITION, TIRE, ADDITIVE AND HYDRAZIDE COMPOUND

(71) Applicant: OTSUKA CHEMICAL CO., LTD., Osaka (JP)

(72) Inventors: Satoshi Hamatani, Higashimurayama (JP); Aya Saiki, Higashimurayama (JP); Shinya Shinozaki, Tokushima (JP); Mifuyu Ueno, Tokushima (JP); Masaki Abe, Tokushima (JP)

(73) Assignee: OTSUKA CHEMICAL CO., LTD., Osaka (JP)

( * ) Notice: Subject to any disclaimer, the term of this patent is extended or adjusted under 35 U.S.C. 154(b) by 472 days.

(21) Appl. No.: 16/322,621

(22) PCT Filed: Aug. 3, 2017

(86) PCT No.: PCT/JP2017/028300
§ 371 (c)(1),
(2) Date: Feb. 1, 2019

(87) PCT Pub. No.: WO2018/025966
PCT Pub. Date: Feb. 8, 2018

(65) Prior Publication Data
US 2019/0177513 A1    Jun. 13, 2019

(30) Foreign Application Priority Data
Aug. 4, 2016    (JP) .................. 2016-153586

(51) Int. Cl.
| | |
|---|---|
| C08K 13/02 | (2006.01) |
| B60C 1/00 | (2006.01) |
| C07C 243/38 | (2006.01) |
| C08K 5/25 | (2006.01) |
| C08L 7/00 | (2006.01) |
| C08L 9/00 | (2006.01) |
| C07C 243/36 | (2006.01) |
| C08K 3/04 | (2006.01) |
| C08K 3/36 | (2006.01) |
| C08K 5/32 | (2006.01) |

(52) U.S. Cl.
CPC .............. *C08K 13/02* (2013.01); *B60C 1/00* (2013.01); *C07C 243/36* (2013.01); *C07C 243/38* (2013.01); *C08K 3/04* (2013.01); *C08K 3/36* (2013.01); *C08K 5/25* (2013.01); *C08K 5/32* (2013.01); *C08L 7/00* (2013.01); *C08L 9/00* (2013.01)

(58) Field of Classification Search
CPC . C08K 13/02; C08K 3/04; C08K 3/36; C08K 5/10; C08K 5/25; C08K 5/32; B60C 1/0016; B60C 11/0008; B60C 1/00; C07C 243/38; C07C 243/36; C08L 7/00; C08L 9/00
See application file for complete search history.

(56) References Cited

U.S. PATENT DOCUMENTS

| | | | |
|---|---|---|---|
| 477,725 A | 6/1892 | Williams, Jr. et al. | |
| 2,716,663 A * | 8/1955 | Heman .................. | C07C 243/38 564/150 |
| 5,476,849 A | 12/1995 | Ulrich et al. | |
| 5,514,676 A | 5/1996 | Ulrich et al. | |
| 8,138,118 B2 | 3/2012 | Bickers et al. | |
| 2005/0037922 A1 | 2/2005 | Bickers et al. | |
| 2006/0235244 A1 | 10/2006 | Wakamori | |
| 2011/0166254 A1 | 7/2011 | Nishimura | |
| 2013/0289165 A1 | 10/2013 | De Landtsheer et al. | |
| 2014/0005320 A1 * | 1/2014 | Weingart ................. | C08K 5/25 524/432 |
| 2020/0079933 A1 | 3/2020 | Saiki et al. | |

FOREIGN PATENT DOCUMENTS

| | | |
|---|---|---|
| CN | 1854123 A | 11/2006 |
| CN | 1829437 B | 3/2011 |
| CN | 110023398 A | 7/2019 |
| EP | 3 392 303 A1 | 10/2018 |

(Continued)

OTHER PUBLICATIONS

English machine translation of JP 2009-221262. (Year: 2009).*
Communication dated Aug. 27, 2019, from the Russian Patent and Trademark Office in application No. 2019103001/05.
Communication dated Jul. 19, 2019 from European Patent Office in counterpart EP Application No. 17837067.2.
International Search Report for PCT/JP2017/028300 dated Nov. 7, 2017 [PCT/ISA/210].
Communication dated Jun. 30, 2020 from the State Intellectual Property Office of the P.R.C. in Application No. 2017800491185.
Communication dated Mar. 18, 2021 from the China National Intellectual Property Administration in CN Application No. 201780049118.5.

(Continued)

*Primary Examiner* — John E Uselding
(74) *Attorney, Agent, or Firm* — Sughrue Mion, PLLC

(57) ABSTRACT

Provided is a rubber composition comprising: a rubber component containing diene-based rubber; a filler, and a compound represented by formula (I) below:

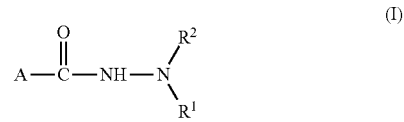

(wherein: A is an aryl group and has at least two polar groups, which may be the same or different from each other; $R^1$ and $R^2$ are each independently at least one substituent selected from a group consisting of a hydrogen atom, an acyl group, an amide group, an alkyl group, a cycloalkyl group, and an aryl group; and further, the substituent may include one or more of O, S, and N atoms), so as to provide a rubber composition excellent in low heat generating property and wear resistance.

14 Claims, No Drawings

(56) References Cited

FOREIGN PATENT DOCUMENTS

| | | | |
|---|---|---|---|
| EP | 3549979 A1 | 10/2019 | |
| JP | 51-14885 A | 2/1976 | |
| JP | 51-14886 A | 2/1976 | |
| JP | 4-136084 A | 5/1992 | |
| JP | 10-139934 A | 5/1998 | |
| JP | 10-330549 A | 12/1998 | |
| JP | 11-292834 A | 10/1999 | |
| JP | 2006-290838 A | 10/2006 | |
| JP | 2006-290839 A | 10/2006 | |
| JP | 2009-221262 * | 10/2009 | ................ C08L 9/00 |
| JP | 2014-501827 A | 1/2014 | |
| RU | 2555024 C2 | 7/2015 | |
| SU | 938595 A1 | 5/1983 | |
| WO | 2012/084821 A1 | 6/2012 | |
| WO | 2017/104467 A1 | 6/2017 | |
| WO | 2018/101368 A1 | 6/2018 | |
| WO | 2018/211932 A1 | 11/2018 | |
| WO | 2018/225478 A1 | 12/2018 | |

OTHER PUBLICATIONS

Notice of Reasons for Refusal dated Aug. 31, 2021 by the Japanese Patent Office in Japanese Application No. 2018-531982.
Communication dated Aug. 6, 2021 by the Brazilian Patent Office in Brazilian Application No. 112019002165-5.

* cited by examiner

RUBBER COMPOSITION, TIRE, ADDITIVE AND HYDRAZIDE COMPOUND

CROSS REFERENCE TO RELATED APPLICATIONS

This application is a National Stage of International Application No. PCT/JP2017/028300, filed on Aug. 3, 2017, which claims priority from Japanese Patent Application No. 2016-153586, filed on Aug. 4, 2016.

TECHNICAL FIELD

The present disclosure relates to a rubber composition, a tire, an additive, and a hydrazide compound.

BACKGROUND

There has been an increasing demand for higher fuel efficiency of automobiles, and tires with lower rolling resistance are desired. For this reason, a rubber composition to be used as a tread of a tire is desired to be low in tan δ and excellent in low heat generating property.

In conventional pneumatic tires, various measures are conceivable for the purpose of achieving low heat generating property, such as to increase the particle size of carbon black in the rubber composition or to reduce the compounding amount of carbon black, which however simultaneously leads to such problems as the reduction of wear resistance of the tread rubber or as the reduction of fracture resistance such as cut resistance or chipping resistance of the rubber.

Therefore, there has been a demand for the development of technology that is capable of improving low heat generating property without impairing other physical properties such as strength.

As one of such technologies, JP2014501827A (PTL 1) discloses, for example, a rubber composition obtained by compounding an elastomer including natural rubber with carbon black and a specific hydrazide compound, for the purpose of improving chemical interaction between the rubber component and carbon black.

CITATION LIST

Patent Literature

PTL 1: JP2014501827A

SUMMARY

Technical Problem

However, the technology disclosed in PTL 1 cannot ensure sufficient low heat generating property, and the low heat generating property needs to be further improved so as to meet the demand for higher fuel efficiency of automobiles. Further, in addition to the improvement of high fuel efficiency, further improvement of wear resistance has also been desired.

It could therefore be helpful to provide a rubber composition excellent in low heat generating performance and wear resistance. It could also be helpful to provide a tire excellent in low heat generating property and wear resistance. Further, it could also be helpful to provide an additive and a novel hydrazide compound capable of exerting excellent low heat generating property and wear resistance, when compounded into the rubber composition.

Solution to Problem

With an aim to overcome the aforementioned problems, we have made intensive studies of a rubber composition including a rubber component and a filler. Then, we have found that hydrazide compounds having a specific structure may be contained in the rubber composition to thereby enhance interaction of the rubber component with carbon black or silica, with the result that more excellent low heat generating property and wear resistance can be realized.

Specifically, the disclosed rubber composition includes: a rubber component containing diene-based rubber; a filler; and a compound represented by the following formula (I):

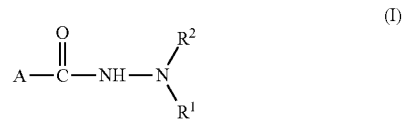

(wherein: A is an aryl group and has at least two polar groups, which may be the same or different from each other; $R^1$ and $R^2$ are each independently at least one substituent selected from a group consisting of a hydrogen atom, an acyl group, an amide group, an alkyl group, a cycloalkyl group, and an aryl group; and further, the substituent may include one or more of O, S, and N atoms).

The aforementioned configuration allows for achieving excellent low heat generating property and wear resistance.

Further, in the disclosed rubber composition, it is preferred that at least one of the polar groups of A in the compound represented by the formula (I) is a hydroxyl group, an amino group, or a nitro group, more preferred that at least one of the polar groups is a hydroxyl group, and particularly preferred that at least two of the polar groups are hydroxyl groups, so as to attain more excellent low heat generating performance and wear resistance.

Further, in the disclosed rubber composition, A in the compound represented by the formula (I) is preferably a phenyl group or a naphthyl group, so as to realize further excellent low heat generating property and wear resistance while being excellent in terms of practical use.

Further, in the disclosed rubber composition, $R^1$ and $R^2$ in the compound represented by the formula (I) are both preferably hydrogen atoms, so as to realize more excellent low heat generating property and wear resistance.

Further, in the disclosed rubber composition, the compound represented by the formula (I) preferably has a molecular weight of 250 or less, so as to realize more excellent low heat generating property and wear resistance.

Still further, in the disclosed rubber composition, the compound represented by the formula (I) preferably has a melting point of 80° C. or higher and lower than 250° C., so as to realize more excellent low heat generating property and wear resistance.

Further, in the disclosed rubber composition, the rubber composition preferably contains 0.05 to 30 parts by mass of the compound represented by the formula (I), with respect to 100 parts by mass of the rubber component, so as to realize more excellent low heat generating property and wear resistance.

Further, in the disclosed rubber composition, the diene-based rubber is preferably natural rubber, so as to realize more excellent low heat generating property and wear resistance.

Still further, in the disclosed rubber composition, the filler preferably includes carbon black and/or silica, so as to realize more excellent low heat generating property and wear resistance.

Further, in the disclosed rubber composition, the rubber composition preferably contains 10 to 160 parts by mass of the filler, with respect to 100 parts by mass of the rubber component, so as to realize more excellent low heat generating property and wear resistance.

Further, in the disclosed rubber composition, the compound represented by the formula (I) is preferably at least one selected from a group consisting of: 2,6-dihydroxybenzohydrazide, 2,3-dihydroxybenzohydrazide, 2,4-dihydroxybenzohydrazide, 2,5-dihydroxybenzohydrazide, 4-amino-2-hydroxybenzohydrazide, 3,5-dihydroxynaphthalene-2-carbohydrazide, 4-amino-3-hydroxynaphthalene-2-carbohydrazide, 3-hydroxy-4-nitronaphthalene-2-carbohydrazide, 1,3-dihydroxynaphthalene-2-carbohydrazide, 2,4,6-trihydroxybenzohydrazide, 2,6-dihydroxy-4-methylbenzohydrazide, and 2-hydroxy-5-nitrobenzohydrazide. Among them 2,6-dihydroxybenzohydrazide, 2,3-dihydroxybenzohydrazide, 3,5-dihydroxynaphthalene-2-carbohydrazide, 4-amino-3-hydroxynaphthalene-2-carbohydrazide, 1,3-dihydroxynaphthalene-2-carbohydrazide, 2,4,6-trihydroxybenzohydrazide, or 2,6-dihydroxy-4-methylbenzohydrazide being further preferred, so as to realize more excellent low heat generating property and wear resistance.

Here, 3,5-dihydroxynaphthalene-2-carbohydrazide and 4-amino-3-hydroxynaphthalene-2-carbohydrazide are novel compounds undescribed in any literature.

The disclosed tire has a feature of using the aforementioned rubber composition.

The tire provided with the aforementioned configuration is capable of realizing more excellent low heat generating property and wear resistance.

The disclosed additive is to be added to a rubber component containing diene-based rubber, and contains the compound represented by the following formula (I):

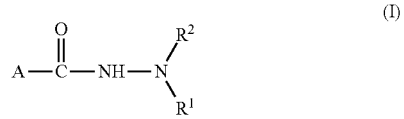

(wherein: A is an aryl group and has at least two polar groups, which may be the same or different from each other; $R^1$ and $R^2$ are each independently at least one substituent selected from a group consisting of a hydrogen atom, an acyl group, an amide group, an alkyl group, a cycloalkyl group, and an aryl group; and further the substituent may include one or more of O, S, and N atoms).

The aforementioned configuration may be provided to improve the rubber composition in terms of low heat generating property and wear resistance.

Advantageous Effect

The disclosed rubber composition as provided herein is excellent in low heat generating property and wear resistance. Further, the present disclosure is capable of attaining tires excellent in low heat generating property and wear resistance. Further, the present disclosure is capable of providing an additive and a novel hydrazide compound capable of exerting excellent low heat generating property and wear resistance, when compounded into the rubber composition.

DETAILED DESCRIPTION

Hereinafter, embodiments of the present disclosure are specifically illustrated by way of example.
(Rubber Composition)
The disclosed rubber composition includes: a rubber component; a filler; and a compound of the following formula (1):

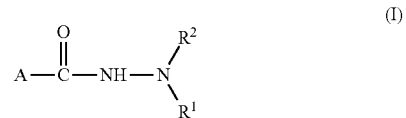

(wherein: A is an aryl group having at least two polar groups, which may be the same or different from each other; $R^1$ and $R^2$ are each independently at least one substituent selected from a group consisting of: a hydrogen atom; an acyl group; an amide group; an alkyl group; a cycloalkyl group; and aryl group, and further the substituent may include one or more of O, S, and N atoms).

Rubber Component

A rubber component to be contained in the disclosed rubber composition is not particularly limited as long as a diene-based rubber is contained.

Examples of the diene-based rubber may include, for example, natural rubber, polyisoprene rubber (IR), styrene-butadiene rubber (SBR), and a poly-butadiene rubber (BR), with natural rubber being preferred, so as to achieve more excellent low heat generating property and wear resistance.

The diene-based rubber may be contained as one kind alone or may be contained as a blend of two or more kinds.

The content of the diene-based rubber in the rubber component is not particularly limited; however, in terms of maintaining excellent low heat generating property, the content may preferably be 80 mass % or more, and more preferably 90 mass % or more.

Filler

The disclosed rubber composition includes a filler, in addition to the aforementioned rubber component.

A filler may be contained along with the aforementioned rubber component and a compound of formula (I) to be described later, to thereby achieve excellent low heat generating property and wear resistance without impairing other physical properties.

Here, the content of the filler, which is not particularly limited, is preferably 10 to 160 parts by mass, and more preferably 30 to 100 parts by mass of the filler with respect to 100 mass parts of the rubber component. The content of the filler may be optimized to thereby achieve more excellent low heat generating property and wear resistance. The content falling below 10 parts by mass may lead to a fear of losing sufficient fracture resistance while the content exceeding 160 parts by mass may lead to a fear of losing sufficient low heat generating property.

Further, examples of the filler may include, without being particularly limited, carbon black, silica, and other inorganic fillers, preferred among them including carbon black and/or silica, so as to obtain more excellent low heat generating property and wear resistance. Here, carbon black and silica may each be contained either alone or in combination.

Here, examples of the carbon black may include carbon black of such grades as GPF, FEF, SRF, HAF, ISAF, IISAF, SAF grades.

Further, examples to be used as the silica may include, without particularly limited, wet silica, dry silica, and colloidal silica etc.

Further, examples to be used as the other inorganic fillers may include an inorganic compound represented by, for example, the following formula (II).

(wherein, M is at least one kind selected from: metal selected from a group consisting of aluminum, magnesium, titanium, calcium, and zirconium; an oxide or hydroxide of these metals and a hydrate thereof, or a carbonate of these metals; and n, x, y, and z each are an integer of 1 to 5, an integer of 0 to 10, an integer of 2 to 5, and an integer of 0 to 10.)

Examples of the inorganic compound of the aforementioned formula (II) may include: alumina ($Al_2O_3$) such as γ-alumina, α-alumina; hydrated alumina ($Al_2O_3 \cdot H_2O$) such as boehmite, diaspore; aluminum hydroxide [$Al(OH)_3$] such as gibbsite, bayerite; aluminum carbonate [$Al_2(CO_3)_3$], magnesium hydroxide [$Mg(OH)_2$], magnesium oxide (MgO), magnesium carbonate ($MgCO_3$), talc ($3MgO \cdot 4SiO_2 \cdot H_2O$), attapulgite ($5MgO \cdot 8SiO_2 \cdot 9H_2O$), titanium white ($TiO_2$), titanium black ($TiO_{2n-1}$), calcium oxide (CaO), calcium hydroxide [$Ca(OH)_2$], magnesium aluminum oxide ($MgO \cdot Al_2O_3$), clay ($Al_2O_3 \cdot 2SiO_2$), kaolin ($Al_2O_3 \cdot 2SiO_2 \cdot 2H_2O$), pyrophyllite ($Al_2O_3 \cdot 4SiO_2 \cdot H_2O$), bentonite ($Al_2O_3 \cdot 4SiO_2 \cdot 2H_2O$), aluminum silicate (such as $Al_2SiO_5$, $Al_4 \cdot 3SiO_4 \cdot 5H_2O$), magnesium silicate (such as $Mg_2SiO_4$, $MgSiO_3$), calcium silicate (such as $Ca_2SiO_4$), calcium aluminum silicate (such as $Al_2O_3 \cdot CaO \cdot 2SiO_2$), calcium magnesium silicate ($CaMgSiO_4$), calcium carbonate ($CaCO_3$), zirconium oxide ($ZrO_2$), zirconium hydroxide [$ZrO(OH)_2 \cdot nH_2O$], zirconium carbonate [$Zr(CO_3)_2$], crystalline aluminosilicates, such as various zeoliates, which include hydrogen for correcting charge, alkali metal, and alkaline earth metal.

Compound of Formula (I)

Then, the disclosed rubber composition includes a compound of the formula (I), in addition to the rubber component and the filler mentioned above.

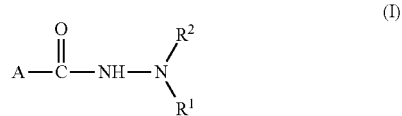

In the formula (I). A represents an aryl group. Here, the aryl group has at least two polar groups at arbitrary positions, where the polar groups may be the same or different from each other, and the positions of the polar groups may be anywhere in the aromatic ring.

Further, in the formula (I), $R^1$ and $R^2$ are each independently at least one substituent selected from a group consisting of: a hydrogen atom; an acyl group; an amide group; an alkyl group; a cycloalkyl group; and aryl group. Further, these substituents may include one or more of O atom, S atom, and N atom.

The compound of the formula (I) above is capable of greatly improving chemical interaction between the rubber component and the filler when compounded in the rubber composition since the aryl group represented by A has a high affinity for the filler such as carbon black and a portion having a hydrazide moiety has a high affinity with the rubber component. In this manner, hysteresis caused by mutual rubbing of the fillers can be reduced, which provides as a result low heat generating property that is extremely excellent than ever before. In addition, the filler is improved in dispersiveness, which can achieve further excellent reinforcement.

Here, examples of the aryl group represented by A in the compound of the aforementioned formula (I) may include an aromatic hydrocarbon group such as a phenyl group, a naphthyl group, an anthryl group, a phenanthryl group, and triphenylenyl group. Among them, a phenyl group or a naphthyl group being preferred as the aryl group, and a phenyl group being more preferred as the aryl group, which shows excellent affinity for the filler to achieve more excellent low heat generating property while reducing the number of aromatic rings, being further preferred so as to be advantages in cost and excellent in terms of practical use.

Further, the aryl group represented by A in the compound of the aforementioned formula (I) may preferably have two or more polar groups. Two or more polar groups disposed in the aromatic ring can provide high affinity for the filler such as carbon black; less than two polar groups may fail to obtain sufficient affinity for the filler, which leads to a fear reducing the low heat generating property of the rubber composition.

Examples of the polar groups may include, without particularly limited: an amino group; an imino group; a nitrile group; an ammonium group; an imide group; an amide group; a hydrazo group; an azo group; a diazo group; a hydroxyl group; a carboxy group; a carbonyl group; an epoxy group; an oxycarbonyl group; a nitrogen-containing heterocyclic group; an oxygen-containing heterocyclic group; a tin-containing group; an alkoxysilyl group; an alkylamino group; and a nitro group. Among them, at least one of the polar groups may be preferably a hydroxyl group, an amino group, or a nitro group, more preferably a hydroxy group, and particularly preferably at least two of the polar groups may be hydroxyl groups, so as to exhibit further excellent affinity for the filler, allowing for further improving the rubber composition in low heat generating property.

Further, as to the hydrazide group binding to A in the compound of the aforementioned formula (I), $R^1$ and $R^2$ are each independently at least one substituent selected from a group consisting of: a hydrogen atom; an acyl group; an amide group; an alkyl group; a cycloalkyl group; and an aryl group. Here, these substituents may include one or more of O, S, and N atoms.

Further, $R^1$ and $R^2$ may preferably a hydrogen atom or an alkyl group from among the aforementioned substituents, and more preferably $R^1$ and $R^2$ are both hydrogen atoms, so as to exhibit high affinity for the rubber component, providing more excellent low heat generating property and wear resistance.

Here, some representative examples of the compound of the aforementioned formula (I) are shown in below.

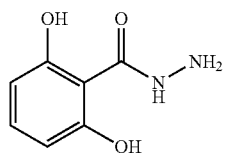

2,6-dihydroxybenzohydrazide

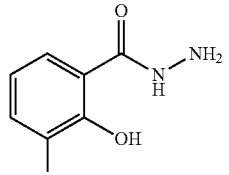

2,3-dihydroxybenzohydrazide

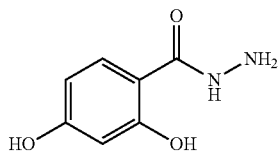

2,4-dihydroxybenzohydrazide

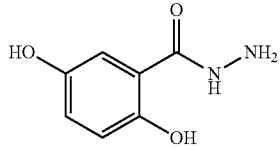

2,5-dihydroxybenzohydrazide

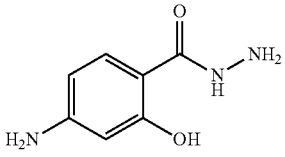

4-amino-2-hydroxybenzohydrazide

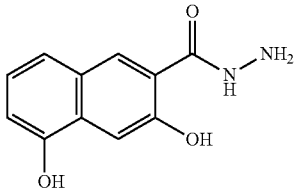

3,5-dihydroxynaphthalene-2-carbohydrazide

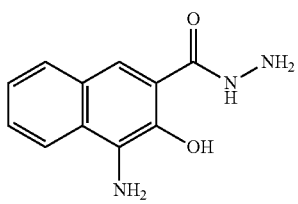

4-amino-3-hydroxynaphthalene-2-carbohydrazide

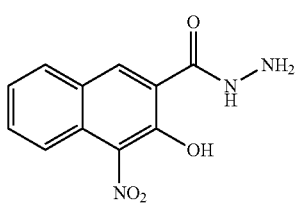

3-hydroxy-4-nitronaphthalene-2-carbohydrazide

-continued

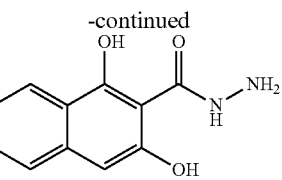

1,3-dihydroxynaphthalene-2-carbohydrazide

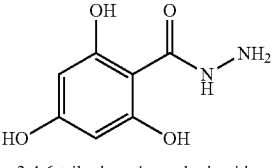

2,4,6-trihydroxybenzohydrazide

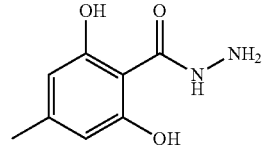

2,6-dihydroxy-4-methylbenzohydrazide

Further, the compound of the formula (I) may have a molecular weight of preferably 250 or less, more preferably 220 or less, and further preferably 180 or less, which exhibits higher affinity for natural rubber, to thereby obtain more excellent low heat generating property and also increase wear resistance.

Further, the compound of the formula (I) above has a melting point which is preferably 80° C. or higher and lower than 250° C. The melting point of the hydrazide compound may thus be lowered to increase affinity for natural rubber, which can provide more excellent low heat generating property and also enhance wear resistance.

Here, the content of the compound represented by the formula (I) in the disclosed rubber composition is preferably be 0.05 to 30 parts by mass, more preferably 0.05 to 10 parts by mass, and particularly preferably 0.05 to 5 parts by mass, with respect to 100 parts by mass of the rubber component. The content being 0.05 parts by mass or more relative to 100 parts by mass of the rubber component provides a desired low heat generating performance, while the content being 30 parts by mass or less can favorably maintain wear resistance and other physical properties such as strength.

Other Components

In addition to the aforementioned rubber component, the filler, and the compound of the aforementioned formula (I), the disclosed rubber composition may include a compounding agent generally used in the rubber industry, such as an antioxidant, a softener, a silane coupling agent, a stearic acid, a zinc oxide, a vulcanization accelerator, a vulcanizer, which may be selected as appropriate without impairing the disclosed object. Commercially available products may be suitably used as these compounding agents.

Method of Producing Rubber Composition

Here, the method of producing the disclosed rubber composition is not particularly limited. For example, a rubber component containing diene-based rubber, a filler, and the compound of the aforementioned formula (I) may be compounded and kneaded by a publicly-known method, to thereby obtain the disclosed rubber composition.

(Tire)

The disclosed tire is configured by using the disclosed rubber composition described above. The disclosed rubber composition may be included as a tire material, to thereby achieve excellent low heat generating property and wear resistance without impairing other physical properties.

The disclosed rubber composition may preferably be used particularly in a tread of the tire. A tire using the disclosed rubber composition as the tread thereof is excellent in low heat generating property and wear resistance.

Here, the disclosed tire is not particularly limited except in that the disclosed rubber composition described above is used in any of the tire members, and the tire may be manufactured according to a usual method. Gas to be filled into the tire may be general air or oxygen partial pressure-adjusted air, or other inert gas such as nitrogen, argon, and helium.

(Additive)

The disclosed additive is to be added to the rubber component containing diene-based rubber, and contains the compound of the following formula (I):

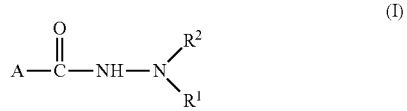

(wherein: A is an aryl group having at least two polar groups which may be the same or different from each other; $R^1$ and $R^2$ are each independently at least one substituent selected from a group consisting of a hydrogen atom, an acyl group, an amide group, an alkyl group, a cycloalkyl group, and an aryl group, and further the substituent may include one or more of O, S, and N atoms).

The additive containing the hydrazide compound of the formula (I) has high affinity for the filler such as carbon black and has high affinity for the rubber component. Thus, when compounded into the rubber composition, the additive is capable of greatly improving chemical interaction between the rubber component and the filler, which results in exhibiting excellent low heat generating property. Further, the filler may be improved in dispersiveness so as to achieve further excellent reinforcement, and the greatly-improved chemical interaction between the rubber component and the filler allows for improving wear resistance. That is, the disclosed additive may be used as a low heat generating agent, a wear resistance imparting agent, a breaking resistance imparting agent, or a viscosity stabilizer, in other words, the disclosed additive encompasses a low loss agent, a wear resistance imparting agent, a breaking resistance imparting agent, or a viscosity stabilizer, each of which contains a hydrazide compound of the formula (I) and is to be added to a rubber component containing a diene-based rubber.

Further, in the disclosed additive, at least one of the polar groups of A in the compound of the aforementioned formula (I) is preferably a hydroxyl group or an amino group or a nitro group, so as to attain more excellent low heat generating property.

Further, in the disclosed additive, A in the compound of the aforementioned formula (I) is preferably a phenyl group or a naphthyl group, so as to attain more excellent low heat generating property while being excellent in terms of practical use.

Further, in the disclosed additive, $R^1$ and $R^2$ in the compound of the aforementioned formula (I) are both preferably hydrogen atoms, so as to attain more excellent low heat generating property and wear resistance.

Further, in the disclosed additive, the compound of the aforementioned formula (I) is preferably be 250 or less in molecular weight, so as to attain more excellent low heat generating property and wear resistance.

Still further, in the disclosed additive, the compound of the aforementioned formula (I) preferably has a melting point of 80° C. or higher and lower than 250° C., so as to attain more excellent low heat generating property and wear resistance.

Further, the disclosed additive may preferably contain 0.05 to 30 parts by mass of the compound of the aforementioned formula (I) with respect to 100 parts by mass of the rubber component, so as to attain more excellent low heat generating property and wear resistance.

In adding the disclosed additive to the rubber component, a compounding agent generally used in the rubber industry, such as an antioxidant, a softener, a silane coupling agent, a stearic acid, a zinc oxide, a vulcanization accelerator, a vulcanizer may be compounded, in addition to a filler such as silica, carbon black, the compounding agent being selected as appropriate without impairing the disclosed object. Commercially available products may be suitably used as these compounding agents.

The rest of the matters as to the disclosed additive are the same as those explained for the disclosed rubber composition described above.

EXAMPLES

The present disclosure is further explained in detail below, with reference to Examples. However, the present disclosure is no way limited by the following Examples.

(Compounds a to k)

Formulae of compounds a to k to be used in Examples are given below.

Also provided in below are: the types of the compounds a to k, together with the melting points thereof and the results of $^1$H-NMR measurements (conditions: 300 MHz, DMSO-$d_6$, δ ppm).

Compound a: 2,6-dihydroxybenzohydrazide 5.29 g of methyl 2,6-dihydroxybenzoate and 3.30 g of 100% hydrazine monohydrate were added to 32 mL of 1-butanol, which was stirred at 117° C. for 15 hours. The reaction mixture was cooled and thereafter filtered for a precipitated solid, which was washed with isopropyl alcohol. The resulting solid was dried in vacuo to obtain 2.85 g of a pale yellow solid of 2,6-dihydroxybenzohydrazide (with the yield of 54%).

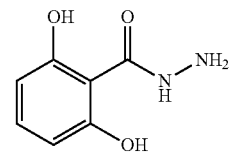 [SMILES: NNC(=O)c1c(O)cccc1O]

(melting point: 198° C. $^1$H-NMR (300 MHz, DMSO-$d_6$. δ ppm): 6.3 (d, 2H), 7.1 (t, 1H), NH(3H) and OH(2H) were undetected)

Compound b: 2,3-dihydroxybenzohydrazide 2.75 g of methyl 2,3-dihydroxybenzoate and 7.00 g of 100% hydrazine monohydrate were added to 1.5 mL of water, which was stirred at 100° C. for 3 hours. The reaction mixture was concentrated, and isopropyl alcohol was added to the precipitated solid for filtering the same, which was washed with isopropyl alcohol. The resulting solid was dried in vacuo to obtain 2.00 g of a pale yellow solid of 2,3-dihydroxybenzohydrazide (with the yield of 73%).

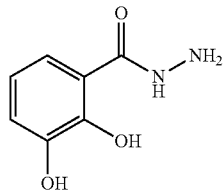 [SMILES: NNC(=O)c1cccc(O)c1O]

(melting point: 223° C., $^1$H-NMR (300 MHz, DMSO-$d_6$, δ ppm): 4.7 (br-s, 2H), 6.7 (m, 1H), 6.9 (m, 1H), 7.2 (m, 1H), 10.1 (br-s, 1H), OH(2H) was undetected)

Compound c: 2,4-dihydroxybenzohydrazide 5.50 g of methyl 2,4-dihydroxybenzoate and 13.4 g of 100% hydrazine monohydrate were added to 3 mL of water, which was stirred at 100° C. for 3 hours. The reaction mixture was concentrated, and isopropyl alcohol was added to the precipitated solid for filtering the same, which was washed with isopropyl alcohol. The resulting solid was dried in vacuo to obtain 4.82 g of a pale yellow solid of 2,4-dihydroxybenzohydrazide (with the yield of 88%).

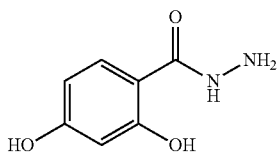 [SMILES: NNC(=O)c1ccc(O)cc1O]

(melting point: 237° C., $^1$H-NMR (300 MHz, DMSO-$d_6$. S ppm): 6.2 (m, 2H), 7.6 (m, 1H), NH(3H) and OH(2H) were undetected)

Compound d: 2,5-dihydroxybenzohydrazide 5.39 g of methyl 2,5-dihydroxybenzoate and 3.29 g of 100% hydrazine monohydrate were added to 32 mL of 1-butanol, which was stirred at 117° C. for 15 hours. The reaction mixture was cooled and thereafter filtered for a precipitated solid, which was washed with isopropyl alcohol. The resulting solid was dried in vacuo to obtain 4.26 g of a pale yellow solid of 2,5-dihydroxybenzohydrazide (with the yield of 79%).

(melting point: 210° C., $^1$H-NMR (300 MHz, DMSO-$d_6$, δ ppm): 4.6 (br-s, 2H), 6.7 (m, 1H), 6.8 (m, 1H), 7.2 (m, 1H), 9.0 (br-s, 1H), 9.9 (br-s, 1H), 11.5 (br-s, 1H))

Compound e: 4-amino-2-hydroxybenzohydrazide 12.0 g of methyl 4-amino-2-hydroxybenzoate and 30.3 g of 100% hydrazine monohydrate were added to 6.6 mL of water, which was stirred at 100° C. for 2 hours. The reaction mixture was concentrated and thereafter added with water, and filtered for a precipitated solid, which was washed with water. The resulting solid was dried in vacuo to obtain 8.68 g of a pale yellow solid of 4-amino-2-hydroxybenzohydrazide (with the yield of 72%).

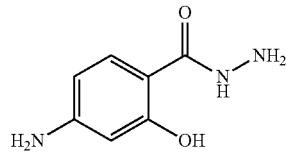

(melting point: 198° C., $^1$H-NMR (300 MHz, DMSO-$d_6$, δ ppm): 4.4 (br-s, 2H), 5.7 (m, 2H), 6.0 (m, 2H), 7.4 (m, 1H), 9.5 (m, 1H), 12.7 (br-s, 1H))

Compound f: 3,5-dihydroxynaphthalene-2-carbohydrazide 43.0 g of 3,5-dihydroxynaphthoic acid and 42.0 mL of concentrated sulfuric acid were added to 860 mL of methanol, which was stirred at 65° C. for 44 hours. The reaction mixture was cooled and thereafter added water and filtered for a precipitated solid, which was washed with water. The resulting solid was dried in vacuo to obtain 44.7 g of a pale yellow solid of methyl 3,5-dihydroxynaphthalene-2-carboxylate (with the yield of 97%).

8.39 g of methyl 3,5-dihydroxynaphthalene-2-carboxylate thus obtained and 5.29 g of 100% hydrazine monohydrate were added to 40.0 mL of butanol, which was stirred at 65° C. for 2 hours. The reaction mixture was concentrated and the precipitated solid was suspended in isopropyl alcohol. The precipitated solid was filtered and washed with isopropyl ether. The solid thus obtained was dried in vacuo to obtain 5.01 g of a pale yellow solid of 3,5-dihydroxynaphthalene-2-carbohydrazide (with the yield of 60%).

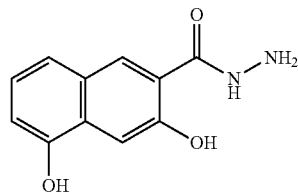 [SMILES: NNC(=O)c1cc2cccc(O)c2cc1O]

(melting point: 219° C., $^1$H-NMR (300 MHz, DMSO-$d_6$, δ ppm): 6.8 (m, 1H), 7.1 (m, 1H), 7.3 (m, 1H), 7.4 (s, 1H), 8.3 (s, 1H), 10.3 (br-s, 2H), NH(3H) was undetected)

Compound g: 4-amino-3-hydroxynaphthalene-2-carbohydrazide 50.0 g of 3-hydroxy-2-naphthoic acid was added to 270 mL of chloroform and cooled by ice-bath, and thereafter 24.3 mL of 60% nitric acid was dropped thereinto, which was stirred for 35 minutes and then filtered for a precipitated solid, which was washed with water and chloroform. The resulting solid was dried in vacuo to obtain 47.7 g of an orange solid of 3-hydroxy-4-nitro-2-naphthoic acid (with the yield of 77%).

12.5 g of 3-hydroxy-4-nitro-2-naphthoic acid thus obtained and 1 mL of concentrated sulfuric acid were added to 200 mL of butanol, which was stirred at 117° C. for 48 hours. The reaction mixture was concentrated and thereafter filtered for a precipitated solid, which was washed with butanol. The resulting solid was dried in vacuo to obtain 7.52 g of a yellow solid of butyl 3-hydroxy-4-nitronaphthalene-2-carboxylate (with the yield of 48%).

28.7 g of butyl 3-hydroxy-4-nitronaphthalene-2-carboxylate thus obtained and 2.90 g of palladium carbon were added to 494 mL of methanol, which was substituted with hydrogen and stirred at room temperature for 8 hours. The reaction mixture was concentrated, and the resulting solid was added with 17.7 g of hydrazine monohydrate and 330 mL of butanol, which was stirred at 75° C. for 13 hours. The reaction mixture was cooled and thereafter filtered for precipitated acid, which was washed with butanol. The resulting solid was dried in vacuo to obtain 21.1 g of a pale yellow solid of 4-amino-3-hydroxynaphthalene-2-carbohydrazide (with the yield of 98%).

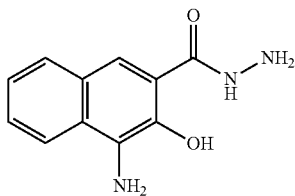 [SMILES: NNC(=O)c1cc2ccccc2c(N)c1O]

(melting point: 181° C., $^1$H-NMR (300 MHz, DMSO-d$_6$, δ ppm): 4.7 (br-s, 2H), 7.3 (m, 1H), 7.4 (m, 1H), 7.6 (m, 1H), 7.7 (s, 1H), 8.0 (m, 1H), 10.4 (br-s, 1H). NH(3H) was undetected)

Compound h: 3-hydroxy-4-nitronaphthalene-2-carbohydrazide 50.0 g of 3-hydroxy-2-naphthoic acid was added to 270 mL of chloroform and cooled by ice-bath, and thereafter 24.3 mL of 60% nitric acid was dropped thereinto, which was stirred for 35 minutes and then filtered for a precipitated solid, which was washed with water and chloroform. The resulting solid was dried in vacuo to obtain 47.7 g of an orange solid of 3-hydroxy-4-nitro-2-naphthoic acid (with the yield of 77%).

12.5 g of 3-hydroxy-4-nitro-2-naphthoic acid thus obtained and 1 mL of concentrated sulfuric acid were added to 200 mL of butanol, which was stirred at 117° C. for 48 hours. The reaction mixture was concentrated and thereafter filtered for a precipitated solid, which was washed with butanol. The resulting solid was dried in vacuo to obtain 7.52 g of a yellow solid of butyl 3-hydroxy-4-nitronaphthalene-2-carboxylate (with the yield of 48%).

17.1 g of butyl 3-hydroxy-4-nitronaphthalene-2-carboxylate thus obtained was dissolved into 175 mL of methanol, and added with 6.28 g of 100% hydrazine monohydrate, which was stirred at 65° C. for 16 hours. The reaction mixture was cooled and thereafter filtered for a precipitated solid, which was washed with methanol. The resulting solid was dried in vacuo to obtain 14.6 g of an orange solid of 3-hydroxy-4-nitronaphthalene-2-carbohydrazide (with the yield of 100%).

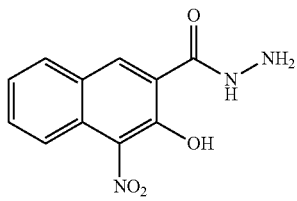 [SMILES: NNC(=O)c1cc2ccccc2c([N+](=O)[O-])c1O]

(melting point: 185° C., $^1$H-NMR (300 MHz, DMSO-d$_6$, δ ppm): 7.1 (m, 1H), 7.4 (m, 2H), 7.8 (m, 1H), 8.4 (m, 1H), NH (3H), and OH(1H) were undetected)

Compound i: 1,3-dihydroxynaphthalene-2-carbohydrazide 2.97 g of magnesium chloride was added to 50 mL of acetonitrile solution containing 5.00 g of diethyl malonate, and cooled by ice-bath. Next, 6.30 g of triethylamine was dropped thereinto and stirred for 30 minutes, and thereafter 4.82 g of phenylacetyl chloride was dropped thereinto, which was then returned to room temperature and stirred for 4.5 hours. The reaction mixture was again cooled by ice-bath, added with 200 mL of 2N hydrochloric acid, extracted with ethyl acetate, and an organic layer was washed with brine. The organic layer was then dried with magnesium sulfate anhydrous and concentrated, and thereafter dried in vacuo. The resulting pale yellow oily residue was cooled by ice-bath, and 15 mL of concentrated sulfuric acid was dropped thereinto, which was returned to room temperature and stirred for 17 hours. The reaction mixture was cooled by ice-bath and slowly added with 35 mL of ice water, and filtered for a precipitated solid, which was washed with water. The resulting solid was dried in vacuo to obtain 6.09 g of a yellow solid of ethyl 1,3-dihydroxynaphthalene-2-carboxylate (with the yield of 84%).

3 mL solution of methanol containing 800 mg of ethyl 1,3-dihydroxynaphthalene-2-carboxylate thus obtained was added with 0.21 g of 100% hydrazine monohydrate at room temperature, which was heated to reflux for 2.5 hours and returned to room temperature to be stirred for 12 hours. The precipitated solid was filtered and the solid thus obtained was washed with methanol and dried in vacuo, so as to obtain 540 mg of an ocher yellow solid of 1,3-dihydroxynaphthalene-2-carbohydrazide (with the yield of 72%).

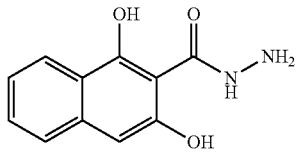 [SMILES: NNC(=O)c1c(O)cc2ccccc2c1O]

(melting point: 205° C., $^1$H-NMR (300 MHz, DMSO-d$_6$, δ ppm): 6.6 (s, 1H), 7.2 (m, 1H), 7.4 (m, 1H), 7.5 (d, 1H), 8.0 (d, 1H), NH (3H), and OH (2H) were undetected)

Compound j: 2,4,6-trihydroxybenzohydrazide 100 mL of acetone solution containing 10.0 g of 2,4,6-trihydroxybenzoic acid monohydrate was added with 2.96 g of sodium carbonate at room temperature and stirred for 10 minutes, which was added with 7.04 g of dimethyl sulfate and heated to 50° C. and stirred for 5 hours. The reaction mixture was concentrated and added with water to be extracted with ethyl acetate, and an organic layer was washed with brine. Further, the organic layer was then dried with magnesium sulfate anhydrous and concentrated, and thereafter the precipitated solid was suspended to be filtered in a mixed solvent of ethyl acetate and hexane and dried in vacuo, so as to obtain 6.03 g of a pink solid of methyl 2,4,6-trihydroxybenzoate (with the yield of 62%).

2.40 g of methyl 2,4,6-trihydroxybenzoate thus obtained was suspended in 10 mL of methanol, added with 0.98 g of 100% hydrazine monohydrate at room temperature and heated to reflux for 1.5 hours, and returned to room temperature to be stirred for 12 hours. The precipitated solid was filtered, and the resulting solid was washed with methanol and dried in vacuo, so as to obtain 960 mg of a beige solid of 2,4,6-trihydroxybenzohydrazide (with the yield of 40%).

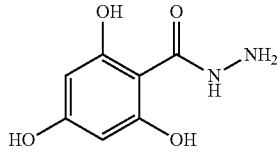 [SMILES: NNC(=O)c1c(O)cc(O)cc1O]

(melting point: 207° C., $^1$H-NMR (300 MHz, DMSO-$d_6$, δ ppm): 4.3 (br-s, 2H), 5.8 (s, 2H), 7.2 (s, 1H), 9.3 (br-s, 1H), 12.3 (br-s, 2H))

Compound k:
2,6-dihydroxy-4-methylbenzohydrazide 50 mL acetone solution containing 5.00 g of 2,6-dihydroxy-4-methyl benzoic acid was added with 1.66 g of sodium carbonate at room temperature and stirred for 10 minutes, and added with 3.94 g of dimethyl sulfate and heated to 50° C. to be stirred for 5 hours. The reaction mixture was concentrated and added with water, which was extracted with ethyl acetate and an organic layer was washed with brine. Further, the organic layer was dried with magnesium sulfate anhydrous and concentrated, and thereafter the precipitated solid was suspended in cold hexane to be filtered, which was dried in vacuo to obtain 4.94 g of a white solid of methyl 2,6-dihydroxy-4-methyl benzoate (with the yield of 91%).

4.50 g of methyl 2,6-dihydroxy-4-methyl benzoate thus obtained was suspended in 12 mL of methanol, added with 1.85 g of 100% hydrazine monohydrate at room temperature, and heated to reflux for 12 hours, which was then returned to room temperature and filtered for a precipitated solid. The resulting solid was washed with methanol and dried in vacuo, so as to obtain 3.09 g of a pink solid of 2,6-dihydroxy-4-methylbenzohydrazide (with the yield of 69%).

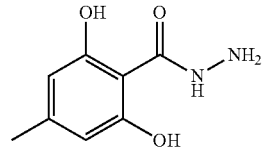

(melting point: 180° C., $^1$H-NMR (300 MHz, DMSO-$d_6$, δ ppm): 2.14 (s, 3H), 5.1 (br-s, 2H), 6.1 (s, 2H), 9.9 (br-s, 1H), 12.5 (br-s, 2H))

Examples 1-1 to 1-11, Comparative Examples 1-1 to 1-2, Examples 2-1 to 2-11, Comparative Examples 2-1 to 2-2

Next, the formulations presented in Tables 1 and 2 were kneaded using a plasto mill to prepare rubber compositions.

Samples of the rubber compositions thus prepared were evaluated for low heat generating property and wear resistance through the following method. The evaluation results are found in Tables 1 and 2.

(1) tan δ (Low Heat Generating Property)

The rubber composition of each sample was vulcanized at 145° C. for 33 minutes to obtain a vulcanized rubber. The vulcanized rubber thus obtained was measured for loss tangent (tan δ) at a temperature of 50° C., with a distortion of 5% and a frequency of 15 Hz, using a visco-elasticity measuring instrument [manufactured by Rheometrics Ltd.].

Here, tan δ was indexed to the value of 100 for Comparative Examples 1-1 and 2-1; a smaller tan δ represents more excellent low heat generating property.

(2) Wear Test (Wear Resistance)

Test pieces were cut out in a disc shape (diameter 16.2 mm×thickness 6 mm) from the vulcanized rubbers thus prepared, and the test pieces were subjected to DIN wear test according to JIS-K6264-2:2005, so as to measure the wear volume (mm$^3$) observed during DIN wear test at room temperature.

Here, the wear volume measured for each sample is displayed as an inverse of the wear volume of the sample which is indexed to 100 for the inverse of the wear volume of Comparative Example 1-1 and Comparative Example 2-1. A larger index value represents a smaller wear volume, which means that the sample is excellent in wear resistance.

TABLE 1

| | | Example | | | | | | | | | | | Comp. Example | |
|---|---|---|---|---|---|---|---|---|---|---|---|---|---|---|
| | | 1-1 | 1-2 | 1-3 | 1-4 | 1-5 | 1-6 | 1-7 | 1-8 | 1-9 | 1-10 | 1-11 | 1-1 | 1-2 |
| formulation (parts by mass) | natural rubber*$^1$ | 100 | 100 | 100 | 100 | 100 | 100 | 100 | 100 | 100 | 100 | 100 | 100 | 100 |
| | carbon black N220*$^2$ | 50 | 50 | 50 | 50 | 50 | 50 | 50 | 50 | 50 | 50 | 50 | 50 | 50 |
| | compound a | 1.0 | — | — | — | — | — | — | — | — | — | — | — | — |
| | compound b | — | 1.0 | — | — | — | — | — | — | — | — | — | — | — |
| | compound c | — | — | 1.0 | — | — | — | — | — | — | — | — | — | — |
| | compound d | — | — | — | 1.0 | — | — | — | — | — | — | — | — | — |
| | compound e | — | — | — | — | 1.0 | — | — | — | — | — | — | — | — |
| | compound f | — | — | — | — | — | 1.0 | — | — | — | — | — | — | — |
| | compound g | — | — | — | — | — | — | 1.0 | — | — | — | — | — | — |
| | compound h | — | — | — | — | — | — | — | 1.0 | — | — | — | — | — |
| | compound i | — | — | — | — | — | — | — | — | 1.0 | — | — | — | — |
| | compound j | — | — | — | — | — | — | — | — | — | 1.0 | — | — | — |

TABLE 1-continued

|  |  | Example |  |  |  |  |  |  |  |  |  |  | Comp. Example |  |
|---|---|---|---|---|---|---|---|---|---|---|---|---|---|---|
|  |  | 1-1 | 1-2 | 1-3 | 1-4 | 1-5 | 1-6 | 1-7 | 1-8 | 1-9 | 1-10 | 1-11 | 1-1 | 1-2 |
|  | compound k | — | — | — | — | — | — | — | — | — | — | 1.0 | — | — |
|  | compound l*[3] | — | — | — | — | — | — | — | — | — | — | — | 1.0 | — |
|  | compound m*[4] | — | — | — | — | — | — | — | — | — | — | — | — | 1.0 |
|  | aromatic oil*[5] | 2.0 | 2.0 | 2.0 | 2.0 | 2.0 | 2.0 | 2.0 | 2.0 | 2.0 | 2.0 | 2.0 | 2.0 | 2.0 |
|  | stearic acid | 2.0 | 2.0 | 2.0 | 2.0 | 2.0 | 2.0 | 2.0 | 2.0 | 2.0 | 2.0 | 2.0 | 2.0 | 2.0 |
|  | antioxidant 6PPD*[6] | 1.0 | 1.0 | 1.0 | 1.0 | 1.0 | 1.0 | 1.0 | 1.0 | 1.0 | 1.0 | 1.0 | 1.0 | 1.0 |
|  | antioxidant TMQ*[7] | 1.0 | 1.0 | 1.0 | 1.0 | 1.0 | 1.0 | 1.0 | 1.0 | 1.0 | 1.0 | 1.0 | 1.0 | 1.0 |
|  | zinc oxide | 3.0 | 3.0 | 3.0 | 3.0 | 3.0 | 3.0 | 3.0 | 3.0 | 3.0 | 3.0 | 3.0 | 3.0 | 3.0 |
|  | vulcanization accelerator CBS*[8] | 0.8 | 0.8 | 0.8 | 0.8 | 0.8 | 0.8 | 0.8 | 0.8 | 0.8 | 0.8 | 0.8 | 0.8 | 0.8 |
|  | sulfur | 1.5 | 1.5 | 1.5 | 1.5 | 1.5 | 1.5 | 1.5 | 1.5 | 1.5 | 1.5 | 1.5 | 1.5 | 1.5 |
| evaluation | tanδ index (low heat generating property) | 70 | 75 | 92 | 91 | 90 | 73 | 71 | 91 | 77 | 72 | 65 | 100 | 88 |
|  | wear index (wear resistance) | 111 | 113 | 105 | 105 | 116 | 109 | 108 | 102 | 107 | 102 | 106 | 100 | 93 |

TABLE 2

|  |  | Example |  |  |  |  |  |  |  |  |  |  | Comp. Example |  |
|---|---|---|---|---|---|---|---|---|---|---|---|---|---|---|
|  |  | 2-1 | 2-2 | 2-3 | 2-4 | 2-5 | 2-6 | 2-7 | 2-8 | 2-9 | 2-10 | 2-11 | 2-1 | 2-2 |
| formulation (parts by mass) | natural rubber*[1] | 100 | 100 | 100 | 100 | 100 | 100 | 100 | 100 | 100 | 100 | 100 | 100 | 100 |
|  | carbon black N220*[2] | 40 | 40 | 40 | 40 | 40 | 40 | 40 | 40 | 40 | 40 | 40 | 40 | 40 |
|  | compound a | 1.0 | — | — | — | — | — | — | — | — | — | — | — | — |
|  | compound b | — | 1.0 | — | — | — | — | — | — | — | — | — | — | — |
|  | compound c | — | — | 1.0 | — | — | — | — | — | — | — | — | — | — |
|  | compound d | — | — | — | 1.0 | — | — | — | — | — | — | — | — | — |
|  | compound e | — | — | — | — | 1.0 | — | — | — | — | — | — | — | — |
|  | compound f | — | — | — | — | — | 1.0 | — | — | — | — | — | — | — |
|  | compound g | — | — | — | — | — | — | 1.0 | — | — | — | — | — | — |
|  | compound h | — | — | — | — | — | — | — | 1.0 | — | — | — | — | — |
|  | compound i | — | — | — | — | — | — | — | — | 1.0 | — | — | — | — |
|  | compound j | — | — | — | — | — | — | — | — | — | 1.0 | — | — | — |
|  | compound k | — | — | — | — | — | — | — | — | — | — | 1.0 | — | — |
|  | compound l*[3] | — | — | — | — | — | — | — | — | — | — | — | 1.0 | — |
|  | compound m*[4] | — | — | — | — | — | — | — | — | — | — | — | — | 1.0 |
|  | silica*[9] | 10 | 10 | 10 | 10 | 10 | 10 | 10 | 10 | 10 | 10 | 10 | 10 | 10 |
|  | silane coupling agent*[10] | 0.8 | 0.8 | 0.8 | 0.8 | 0.8 | 0.8 | 0.8 | 0.8 | 0.8 | 0.8 | 0.8 | 0.8 | 0.8 |
|  | aromatic oil*[5] | 2.0 | 2.0 | 2.0 | 2.0 | 2.0 | 2.0 | 2.0 | 2.0 | 2.0 | 2.0 | 2.0 | 2.0 | 2.0 |
|  | stearic acid | 2.0 | 2.0 | 2.0 | 2.0 | 2.0 | 2.0 | 2.0 | 2.0 | 2.0 | 2.0 | 2.0 | 2.0 | 2.0 |
|  | antioxidant 6PPD*[6] | 1.0 | 1.0 | 1.0 | 1.0 | 1.0 | 1.0 | 1.0 | 1.0 | 1.0 | 1.0 | 1.0 | 1.0 | 1.0 |
|  | antioxidant TMQ*[7] | 1.0 | 1.0 | 1.0 | 1.0 | 1.0 | 1.0 | 1.0 | 1.0 | 1.0 | 1.0 | 1.0 | 1.0 | 1.0 |
|  | zinc oxide | 3.0 | 3.0 | 3.0 | 3.0 | 3.0 | 3.0 | 3.0 | 3.0 | 3.0 | 3.0 | 3.0 | 3.0 | 3.0 |
|  | vulcanization accelerator CBS*[8] | 0.8 | 0.8 | 0.8 | 0.8 | 0.8 | 0.8 | 0.8 | 0.8 | 0.8 | 0.8 | 0.8 | 0.8 | 0.8 |
|  | sulfur | 1.5 | 1.5 | 1.5 | 1.5 | 1.5 | 1.5 | 1.5 | 1.5 | 1.5 | 1.5 | 1.5 | 1.5 | 1.5 |
| evaluation | tanδ index (low heat generating property) | 76 | 79 | 94 | 95 | 94 | 74 | 72 | 92 | 76 | 75 | 69 | 100 | 90 |
|  | wear index (wear resistance) | 108 | 109 | 105 | 105 | 113 | 112 | 111 | 103 | 115 | 103 | 107 | 100 | 96 |

*[1]RSS#1
*[2]"#80" manufactured by Asahi Carbon Co., Ltd.
*[3]3-hydroxy-2-naphthoic hydrazide, manufactured by Tokyo Chemical Industry Co., Ltd.
*[4]isophthalic dihydrazide, manufactured by Tokyo Chemical Industry Co., Ltd.
*[5]"A/O MIX", manufactured by Sankyo Yuka Kogyo K.K.
*[6]N-(1,3-dimethylbutyl)-N'-phenyl-p-phenylenediamine, manufactured by Ouchi Shinko Chemical Industrial, under the trade name of "Noclack-6C"
*[7]2,2,4-trimethyl-1,2-dihydroquinoline polymer, manufactured by Ouchi Shinko Chemical Industrial, under the trade name of "Noclack-224"
*[8]N-cylohexyl-2-benzothiazole sulfeneamide, manufactured by Sanshin Chemical Industry Co., Ltd., under the trade name of "Sanceler CM"
*[9]"Nipsil AQ" manufactured by Tosoh Silica Corporation
*[10]"Si75" manufactured by Evonic Industries Referring to the results of Table 1, the rubber compositions of Examples can all be found to exhibit excellent low heat generating property and wear resistance.

INDUSTRIAL APPLICABILITY

The disclosed rubber composition is excellent in low heat generating property and wear resistance. Further, the disclosed tire is also excellent in low heat generating property and wear resistance. Still further, the disclosed additive and novel hydrazide compound are capable of exhibiting excellent low heat generating performance and wear resistance when compounded in a rubber composition.

The invention claimed is:
1. A rubber composition comprising: a rubber component containing diene-based rubber; a filler, and a compound represented by the following formula (I):

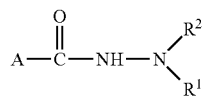
(I)

(wherein: A is a phenyl group or a naphthyl group and has at least two polar groups, which is at least one of the functional group selected from a group consisting of a hydroxyl group, an amino group and a nitro group and at least one of the functional group is the hydroxyl group, and which may be the same or different from each other; $R^1$ and $R^2$ are each independently at least one substituent selected from a group consisting of a hydrogen atom, an alkyl group, a cycloalkyl group, and an aryl group; and further, the substituent may include at least one of O, S, and N atoms).

2. The rubber composition according to claim 1, wherein at least two of the polar groups of A in the compound represented by the formula (I) are hydroxyl groups.

3. The rubber composition according to claim 1, wherein $R^1$ and $R^2$ in the compound represented by the formula (I) are both hydrogen atoms.

4. The rubber composition according to claim 1, wherein the compound represented by the formula (I) has a molecular weight of 250 or less.

5. The rubber composition according to claim 1, wherein the compound represented by the formula (I) has a melting point of 80° C. or higher and lower than 250° C.

6. The rubber composition according to claim 1, wherein the rubber composition contains 0.05 to 30 parts by mass of the compound represented by the formula (I), with respect to 100 parts by mass of the rubber component.

7. The rubber composition according to claim 1, wherein the diene-based rubber is natural rubber.

8. The rubber composition according to claim 1, wherein the filler includes carbon black and/or silica.

9. The rubber composition according to claim 1, wherein the rubber composition contains 10 to 160 parts by mass of the filler, with respect to 100 parts by mass of the rubber component.

10. The rubber composition according to claim 1, wherein the compound represented by the formula (I) is at least one selected from a group consisting of: 2,6-dihydroxybenzohydrazide; 2,3-dihydroxybenzohydrazide; 2,4-dihydroxybenzohydrazide; 2,5-dihydroxybenzohydrazide; 4-amino-2-hydroxybenzohydrazide; 3,5-dihydroxynaphthalene-2-carbohydrazide; 4-amino-3-hydroxynaphthalene-2-carbohydrazide; 3-hydroxy-4-nitronaphthalene-2-carbohydrazide; 1,3-dihydroxynaphthalene-2-carbohydrazide; 2,4,6-trihydroxybenzohydrazide; 2,6-dihydroxy-4-methylbenzohydrazide; and 2-hydroxy-5-nitrobenzohydrazide.

11. A tire formed by using the rubber composition according to claim 1.

12. The rubber composition according to claim 2, wherein $R^1$ and $R^2$ in the compound represented by the formula (I) are both hydrogen atoms.

13. The rubber composition according to claim 2, wherein the compound represented by the formula (I) has a molecular weight of 250 or less.

14. The rubber composition according to claim 2, wherein the compound represented by the formula (I) has a melting point of 80° C. or higher and lower than 250° C.

* * * * *